United States Patent [19]

Carlson et al.

[11] Patent Number: 5,149,623

[45] Date of Patent: Sep. 22, 1992

[54] RAPID, EASY, AND ECONOMICAL SCREENING TEST FOR ANTIBODIES TO HUMAN IMMUNODEFICIENCY VIRUS

[75] Inventors: James R. Carlson; Steve C. Mertens, both of Davis; Joann L. Yee, Sacramento, all of Calif.

[73] Assignee: Virotest, Inc., Lodi, Calif.

[21] Appl. No.: 303,819

[22] Filed: Feb. 1, 1989

[51] Int. Cl.$^5$ .................. C12Q 1/70; C12Q 1/00; G01N 33/53

[52] U.S. Cl. ..................... 435/5; 435/7.92; 435/974; 435/975; 435/7.2

[58] Field of Search .......... 435/5, 7.92, 974, 975, 435/7.2

[56] References Cited

U.S. PATENT DOCUMENTS

| | | | |
|---|---|---|---|
| 4,808,536 | 2/1989 | Chang et al. | 435/5 |
| 4,816,387 | 3/1989 | Osther | 435/5 |
| 4,885,235 | 12/1989 | Osther et al. | 435/5 |
| 4,886,742 | 12/1989 | Kortright et al. | 435/5 |

FOREIGN PATENT DOCUMENTS

56803/86 4/1987 Australia.

OTHER PUBLICATIONS

Archibald et al, "Salivary Antibodies as a Means of Detecting Human T Cell Lymphotropic Virus Type III/Lymphadenopathy-Associated Virus Infection," J. of Clin. Microbiol., 24(5) 873-875 (1986).

Lin et al, "Rapid Dot Enzyme Immunoassay for the Detection of Antibodies to Cytomegalovirus," J. of Clin. Microbiol., 24:7-11 (1986).

Chang et al, "Detection of Antibodies to Human T-Cell Lymphotropic Virus-III (HTLV-III) with an Immunoassay Employing a Recombinant Escherichia Coli-derived Viral Antigenic Peptide," Bio/Technology, 3:905-909 1985.

Parry et al., "Sensitive Assays for Viral Antibodies in Saliva: an Alternative to tests on Serum," Lancet 72-75 (Jul. 1987).

Kiefer et al., "Normalized Enzyme-Linked Immunosorbent Assay for determining Immunoglobin G Antibodies to Cytomegalovirus," J. Clinical Microbiol. 18:33-39 (1983).

Carlson, J. R., et al., "AIDS Serology Testing in Low- and High-Risk Groups," JAMA, 253:3405-3408 (1985).

Carlson, et al., "Rapid, Easy, and Economical Screening Test for Antibodies to Human Immunodeficiency Virus," The Lancet, pp. 361-362, Feb. 14, 1987.

Primary Examiner—Christine M. Nucker
Assistant Examiner—David R. Preston
Attorney, Agent, or Firm—Townsend and Townsend

[57] ABSTRACT

A new dot enzyme immunoassay (EIA) with a conserved portion of the envelope protein of the human immunodeficiency virus (HIV) as antigen has been designed for use in areas with few laboratory facilities and by personnel with little laboratory experience. Sera were tested in 263 subjects who had AIDS or AIDS-related complex or were at -risk or not-at-risk of AIDS from the USA, Africa, and Asia/Oceania. The dot EIA was 100% sensitive in the American subjects, and there were only 2 false negatives in the others, both of which were negative by commerical EIA. The test is simple to perform, economical, rapid (30 min), and stable.

8 Claims, No Drawings

RAPID, EASY, AND ECONOMICAL SCREENING TEST FOR ANTIBODIES TO HUMAN IMMUNODEFICIENCY VIRUS

BACKGROUND OF THE INVENTION

1. Field of the Invention

This invention relates to a new dot enzyme immunoassay (EIA) with a conserved portion of the envelope protein of the human immunodeficiency virus (HIV) as antigen. The immunoassay has been designed for use in areas with few laboratory facilities and by personnel with little laboratory experience. The test is simple to perform, economical, rapid (30 min), and stable.

2. Information Disclosure

Immunoassays for the detection of human antibodies against HIV are currently being used in laboratories to diagnose individuals infected with the AIDs virus. Carlson, J.R. et al. AIDS Serology Testing in Low- and High-Risk groups, JAMA, 253:3405-3408 (1985).

HIV antibodies have been found in saliva from infected individuals. The concentration of antibodies in saliva was 50 times less than in serum and a need for a reliable yet simple assay system for detection of HIV antibodies in saliva has been declared. Archibald, D.W., et al., "Salivary Antibodies as a Means of Detecting Human T Cell Lymphotropic Virus Type III/Lymphadenopathy-Associated Virus Infection," J. of Clin. Microbiol., Vol. 24(5) 873-875 (1986).

The dot enzyme immunoassay is known. Lin T-M, and Halbert, S.P., Rapid Dot Enzyme Immunoassay for the Detection of Antibodies to Cytomegalovirus, J. of Clin. Microbiol. 24:7-11 (1986).

The preferred antigen for use in the disclosed immunoassay is described by Chang, T.W. et al., Detection of Antibodies to Human T-Cell Lymphotropic Virus-III (HTLV-III) with an Immunoassay Employing a Recombinant Escherichia Coli-derived Viral Antigenic Peptide, Bio/Technology 3:905-909 (1985).

SUMMARY OF THE INVENTION

Disclosed herein is an improved method for conducting an immunoassay for the detection of antibodies against the human immunodeficiency virus in clinical samples consisting of reagents stable at temperatures between 4° C. and 39° C. comprising:

(a) immobilizing antigen to a solid support said antigen able to bind antibodies directed against human immunodeficiency virus;

(b) reacting immobilized antigen from step (a) with clinical samples containing antibodies directed against human immunodeficiency virus to form antigen/antibody complexes;

(c) reacting the antigen/antibody complexes with enzyme-labelled antihuman antibodies to form a sandwich complex;

(d) separating unbound labelled antihuman antibodies from the sandwich complex; and (e) reacting the sandwich complex with a compound able to act as a substrate for the enzyme label such that the enzymatic reaction can be colorimetrically monitored.

In the preferred method, one optionally washes the antigen/antibody complexes of step (b) with washing solutions comprising detergents to remove unbound antibody.

The preferred label is alkaline phosphatase and the preferred substrate for alkaline phosphatase is 5-bromo-4-chloro-3-indolyl phosphate toluidine.

In keeping with the objective of this assay to be simple and reliable, an embodiment of the assay requires that the solid support be comprised of an inert flat surface upon which a multiplicity of separate areas have had spots of antigen immobilized thereto. More specifically there is described herein an immunoassay wherein the flat inert solid support is divided into a multiplicity of quadrants each having an aliquot of antigen immobilized to a portion of the surface within each quadrant.

The preferred antigen is the HIV antigen Peptide 121. These immunoassays can detect HIV antibodies in clinical samples of whole blood, sera or saliva.

In keeping with the objective of economy, one of the buffered saline solutions used as a diluent for the clinical samples contains nonfat dry milk as an inhibitor of nonspecific binding. The nonfat milk is preferably at a concentration of between 2-10% of the total weight of the solution. The preferred diluents contain salts of phosphate as buffers.

Where the clinical samples are whole blood, the buffered saline solutions used as a sample diluent preferably contains a cationic surfactant.

Also disclosed herein are immunoassay kits embracing the immunoassays described above.

DETAILED DESCRIPTION

Current tests for antibodies to the human immunodeficiency virus (HIV) require both technical skills and expensive equipment. Both are scarce in Africa and in other developing countries. The disclosed immunoassay is designed for use in such areas under nonlaboratory conditions.

There is an obvious need for a test such as the dot EIA in areas with epidemic HIV infections and AIDS that do not have laboratory facilities. In some African cities, between 6 and 18% of blood donors are infected with HIV and therefore are probably transmitters of HIV infection. Due to technical and economic constraints, few transfusion services in Africa are screening donor blood for antibodies against HIV. The dot EIA test disclosed herein will be useful in both blood product screening and in initial clinical assessment in such areas. If made widely available, the disclosed assay is expected to help limit the spread of HIV.

In addition to being simple and economical, the described assay is thermal insensitive. It operates well at temperature ranges of 4°-40° C. and particularly stable at temperatures of 22° C.-40° C., which effectively eliminates the need for refrigerated conditions.

The disclosed assay is particularly well suited to the detection of HIV antibodies in saliva. It was previously thought that only more expensive, complex tests could be used for reliably detecting HIV antibodies in saliva. The combination of reliability, economy and simplicity makes this assay particularly valuable for home use and for use in uncontrolled environments.

The immunoassay takes place entirely on a solid support upon which is immobilized an antigen specifically reactive with human antibodies against HIV. The solid support is typically inert, and slightly hydrophobic. Glass or plastic will work with polystryene being preferred. To facilitate the reading of positive and negative results, the support may be tinted white or if the support is transparent a piece of white material may be placed behind the support to enhance the contrast.

Antigens may be any HIV specific protein or glycoprotein. It is preferred that the antigen be sufficiently conserved such that its epitopes are present in a majority of HIV varients. The use of conserved antigens assures a high level of reliability in that conserved antigens will react with the greatest number of HIV infected samples. Such antigens include whole (disrupted) virions, p24 and gp 120/160. The preferred antigen is designated peptide 121 and is an 82 amino acid residue protein encoded by a viral gene segment from the env- lor region and is thought to be a part of the gp41 protein. This protein has been reported to be highly antigenic and is believed to be a conserved region common to most HIV varients. The peptide sequence is Glu Ala Gln Gln His Leu Leu Gln Leu Thr Val Trp Gly Ile Lys
1                   5                        10                       15

Gln Leu Gln Ala Arg Ile Leu Ala Val Glu Arg Tyr Leu Lys Asp
            20                       25                       30

Gln Gln Leu Leu Gly Ile Trp Gly Cys Ser Gly Lys Leu Ile Cys
            35                       40                       45

Thr Thr Ala Val Pro Trp Asn Ala Ser Trp Ser Asn Lys Ser Leu
            50                       55                       60

Glu Glu Ile Trp Asn Asn Met Thr Trp Met Glu Trp Asp Arg Glu
            65                       70                       75

Ile Asn Asn Tyr Thr Ser Leu
            80

Bio/Technology 3:905-908 (1985).

The antigen is prepared by spotting an aliquot of antigen containing solution upon one of several regions on the inert support. The amount of antigen is not critical except that identical quantities are necessary in each test region to ensure reproducibility. Typically the antigen is in a buffered solution that is physiologically compatible and preserves the natural secondary and tertiary structure of the antigen. The amount of antigen per test site is between 1 and 10 ug/site perferably between 3 and 7 ug/site. The antigen can be dried at room temperature or at higher temperatures of up to 58° C. The supports can be then stored at room temperature as long as the conditions are relatively dry. A dessicant is helpful.

Clinical samples would include any biological material believed to possibly contain HIV antibodies of human origin. Such samples would include whole blood, plasma, saliva, etc. The samples are typically diluted using a physiologically compatible buffer in the pH range of 6.5-7.5 and salt concentrations of between 0.01 and 0.5 M. Preferred buffers include saline solutions of Tris-HCl and sodium phosphate. Whole blood samples are diluted with buffers that also contain cationic detergents to facilitate lysis of whole blood cells. Examples of cationic detergents useful in the disclosed assays include Hematall LA-Hgb Reagent from Fischer Scientific Headquarters, Springfield, NJ, S/P Lysing Hemoglobin Reagent from American Scientific Products, McGraw, Il. and ZAP from Coulter Corp., Hialeah, Fl. The buffering diluents also contain blocking agents to inhibit non-specific binding of antibodies. Typical blocking agents include normal serum from the same species of animal from which the labelled antibodies are derived such as normal goat serum. A preferred blocking agent useful in this invention is non-fat milk protein. Such protein is economical, stable and more versatile than other blocking agents.

The diluted samples are first placed upon the immobilized antigen and allowed to react. Typically the reaction conditions can vary widely. The tests are generally effective from between 4° C. and 40° C. at varying degrees of humidity. Typically the reaction times increase with increasing temperature and range from between 3 minutes and 1 hour.

After exposure to the sample, the supports are washed with a wash solution compatible with or identical to the diluent used to dilute the samples. The washing removes the unbound antibodies not reactive to the antigen. Washing solutions are typically a buffered saline solution containing small amounts of nonionic detergents. The buffer/salt system is similar to the buffer/salt systems used for dilution but not necessarily identical to it.

The washed supports are then tapped dry or allowed to completely dry at between 20° to 40° C. The sample treated antigen spots are then exposed to solutions of serum containing anti-human antibodies. These anti-human antibodies can be derived from a variety of animal sources such as horse, goat, rabbit or mouse. The preferred anti-human antibodies are directed against the heavy chain of human immunoglobulin G (IgG). Such antibodies are commercially available or can be immunospecifically purified using affinity chromatography. The antibodies can be labelled with any enzyme typically used in immunoassays such as alkaline phosphatase and horseradish peroxidase. For this invention the enzyme is preferably temperature stable not easily denatured while in aqueous solution. Therefore enzymes as stable or more stable than alkaline phosphatase are preferred. For a general review of enzymatic immunoassays, see Walls K.W., Enzyme Immunoassays, in Molecular Immunology Ed. by Atassi, M.Z. et al., Marcel Decker Inc., New York, pps. 427-445 (1984). In keeping with the objective of simplicity, the preferred enzymes produce distinct colorimetric reactions with appropriate substrates and are stable without refrigeration. The preferred enzyme substrate combination is alkaline phoshatase with substrate, 5-bromo-4-chloro-3-indolyl phosphate toluidine salt (Sigma Chem. Co., St. Louis, Mo.). J. Clin. Microbiol. 24:7-11 (1986). This combination produces a distinct insoluble blue deposit clearly visible to the naked eye.

The presence or absence of a color reaction is determinative of the presence or absence of HIV specific antibodies in a clinical sample from a human patient. To be precise each support should contain positive and negative controls.

Kits embracing the immunoassay described above will include the following components:

1. Package insert describing the purpose of the kit and instructions for using the kit.

2. One or more supports of polystyrene plastic (white) having delineated regions numbered to designate the location of antigen and negative controls (HIV antigen-free). The supports can be sealed in a plastic wrap to prevent damage due to excessive humidity.

3. Sample diluents in either dry or liquid form. The diluents may contain the detergents and blocking agents or these may be in separate containers. The exact make up of the diluents will depend upon the skill level of the anticipated users and the conditions under which they are expected to be working. In some kits it is conceivable that sterile water will be provided and in other kits it will be left to the tester to provide sterile water In conditions where accurate measurements are not convenient, the kit can be designed to provide all the diluent components for use as is.

4. The labelled anti-human serum is provided in either a dry or stable liquid form.

5 The substrate is provided in either dry or stable liquid form.

6. A sample of sera containing antibodies to the selected HIV antigen for a positive control 7. A sample of normal sera for a negative control.

8. Wash solutions in either dry or liquid form.

9. Miscellaneous labelling devices, washing devices and containers for the various reagents are optionally included.

The following examples are provided for illustration and are not to be construed as a limitation upon the claims.

EXAMPLES

EXAMPLE 1

A. Methodology

In our assay, white opaque high-impact 'Polystyrene' cards were divided into 1 cm$^2$ squares with black ink. Drops of HIV antigen derived from a recombinant Escherichia coli HIV envelope protein, peptide 121 (Ag 121; Centocor, Malvren, Pa), at a concentration of 5 $\mu$l were spotted in the center of each square and dried at 56° C. for 30 min. Prepared cards were stored at room temperature. All other procedures were done at room temperature. A drop of test serum at an optimum dilution in phosphate buffered saline (pH 7.4) with 10% normal goat serum (PBSNG) was added to cover each dried dot and incubated for 5 min without agitation. Thorough washing with 1 mM Tris-HCl (pH 7.4) in normal saline with 0.05% Tween-20 removed unbound antibodies. A drop of alkaline phosphatase-conjugated goat antihuman IgG (TAGO Inc, Burlingame, Ca.) diluted 1 in 400 in PBSNG was added to cover each dot and incubated for 15 min. The card was then washed thoroughly and each dot was covered by a drop of 5-bromo-4-chloro-3-indolyl phosphate toluidine (Sigma) in 2-amino-2-methylpropanol buffer (pH 10.25) for 3-5 min. The test was read at 3-5 min when the positive control showed full color development. A bright blue color in the dried dot (sometimes paler in the center) developed in positive samples. Negative samples had virtually no color. After a final wash, the dried card provided a stable record of the results.

B. Subjects

The serum panel included a wide range of ill and healthy subjects from America, Africa, and Asia/Oceania. Sera from America were obtained from patients with AIDS or AIDS-related complex (ARC), from at-risk groups (homosexuals, hemophiliacs, intravenous drug abusers), and from subjects with no known HIV exposure. Eighteen sera that were repeatedly positive in the Abbott EIA system but which were negative by WB were also tested. Sera from Africa were obtained from subjects from West, Central, and East African countries. The sera tested included 2 from patients with AIDS, 5 with persistent generalized lymphadenopathy, 21 hospital patients without AIDS, 38 healthy blood donors, 7 patents with endemic Kaposi's sarcoma, and 6 age-matched controls, 9 lymphoma and leukaemia patients, 5 women attending an antenatal clinic, and 10 sera from people in an area with a high prevalence of parasitic diseases, a group which had previously yielded a high frequency of false-positive EIA reactions.

C. Results

The sensitivity of the dot test was good over a wide range of serum dilution. Optimum concentrations of reagents for specificity were determined by checkerboard titrations. A 1 in 100 dilution of serum or plasma was adequate for specimens of all types from America. However, specimens from Africa and Asia/Oceania were diluted to 1 in 200 to reduce nonspecific reactions since more than 10% of WB negative sera were nonspecifically reactive at a 1 in 50 dilution.

Table 1 shows that for the 118 American sera there was agreement between the dot EIA and WB in all but one sample. All WB positive sera were dot EIA positive, i.e., the dot EIA was 100% sensitive with this panel. One WB negative specimen (from a patient with haemophlia) was dot EIA positive.

There was a 100% correlation between the commercial EIA and WB.

Among the 145 sera from Africa and Asia/Oceania all but 2 WB positive sera were positive in the dot EIA. These 2 false negatives were from blood donors and were negative by commercial EIA. Both showed weak reactivity to p24 and no reactivity to gp41 by WB, making the results difficult to interpret. 2 other dot EIA, commercial EIA, and WB positive sera were also p24 positive, gp41 negative. No dot EIA false positives were observed; however, the commercial EIA yielded four false positives compared with WB.

There was good reproducibility of results with DOT EIA: in eight replicate tests, ten WB positive sera were always positive and ten negative sera were always negative. The tests were done in two laboratories by six people with laboratory experience varying from none to much.

The reagents were stable at room temperature (22-25° C.) for at least two months. Cards coated with the recombinant AG 121 and prepared reagents were tested each week for eight weeks without any change in reactivity. The estimated cost of the dot EIA was $0.015 per test for all reagents and supplies excluding the antigen. The cost of the antigen, AG 121, has not been determined by the manufacturer.

EXAMPLE 2

Following the procedure as described in example 1 and substituting 5% non-fat dry milk for the 10% normal goat serum.

EXAMPLE 3

Using the method of Example 1, saliva specimens from 139 individuals were assayed for HIV antibodies. The saliva was diluted to an optimal dilution in phosphate buffered saline with 10% normal goat serum to cover each dried antigen dot. The samples were incubated for 5 minutes at room temperature and washed with 1.0 m mol/1 "tris" in normal saline with 0.05% Tween-20. A drop of a 1:400 dilution of alkaline phosphatase-conjugated goat anti-human IgG from Tago, Inc. (Burlingame, Ca. USA) was added and incubated for 15 minutes at room temperature. The plastic plates were washed again and a drop of 5-bromo-4-chloro-3-indolyl phosphate toluidine in 2-amino-2-methylpropanol buffer (pH 10.25) was added for three to five minutes. The test was read when a positive control spot was fully developed as a bright blue color. Negative controls are colorless.

The results of the saliva test was correlated with the serum samples from the same individuals. There was 98.4% agreement between the Dot EIA using saliva as a specimen and the standard methods using serum. The Dot EIA yielded only one false positive and one false negative for this preliminary test.

EXAMPLE 4

A kit for conducting the immunoassay of Example 2 in plasma samples or saliva samples comprising:

1. A package insert detailing the purpose and instructions for using the kit.
2. White opaque high-impact Polystyrene cards divided into 1 cm² squares with black ink and containing 5 µg of HIV antigen derived from a recombinant Escherichia coli HIV envelope protein, peptide 121 spotted in the center of each square. Prepared cards are sealed in a plastic container.
3. Containers of sterile diluents of phosphate buffered saline (pH 7.4) with 5% dry fat milk.
4. Containers of sterile washing buffers of 1 mM Tris-HCl in normal saline with 0.05% 'Tween-20'.
5. A vial of Alkaline phosphatase-conjugated goat antihuman IgG diluted 1 in 400 in phosphate buffered saline normal goat serum.
6. A vial of 5-bromo-4-chloro-3-indolyl phosphate toluidine (Sigma) in 2-amino-2-methylpropanol buffer (pH 10.25)

TABLE 1

CORRELATION OF DOT EIA, COMMERCIAL EIA, AND WESTERN BLOT RESULTS

| Group | Dot EIA | WB + | WB − | Commercial EIA | WB + | WB − |
|---|---|---|---|---|---|---|
| US sera | | | | | | |
| AIDS (n = 20) | + | 20 | 0 | + | 20 | 0 |
|  | − | 0 | 0 | − | 0 | 0 |
| ARC (n = 20) | + | 20 | 0 | + | 20 | 0 |
|  | − | 0 | 0 | − | 0 | 0 |
| High risk (n = 40) | + | 20 | 1 | + | 20 | 0 |
|  | − | 0 | 19 | − | 0 | 20 |
| Healthy heterosexuals (n = 20) | + | 0 | 0 | + | 0 | 0 |
|  | − | 0 | 20 | − | 0 | 20 |
| Abbott EIA (n = 18) false positives* | + | 0 | 0 | + | 0 | 0 |
|  | − | 0 | 18 | − | 0 | 18 |
| NM-US sera | | | | | | |
| Solomon Islands (n = 18) | + | 0 | 0 | + | 0 | 3 |
|  | − | 0 | 18 | − | 0 | 15 |
| Indonesia (n = 12) | + | 0 | 0 | + | 0 | 1 |
|  | − | 0 | 12 | − | 0 | 11 |
| Malaysia (n = 12) | + | 0 | 0 | + | 0 | 0 |
|  | − | 0 | 12 | − | 0 | 12 |
| Africa (n = 103) | + | 48 | 0 | + | 48 | 0 |
|  | − | 2** | 53 | − | 2** | 53 |

*Repeatedly positive in Abbott EIA system but WB negative.
**Same two sera.

What is claimed is:

1. A method for conducting a thermal insensitive immunoassay for the detection of antibodies against the human immodeficiency virus in saliva said method comprising:
   (a) immobilizing antigen peptide of 121 of Seq. ID NO. 1 to a solid support;
   (b) reacting immobilized antigen from step (a) with saliva samples suspected of containing antibodies directed against human immunodeficiency virus to form antigen/antibody complexes;
   (c) washing the antigen/antibody complexes of step (b) with washing solutions comprising detergents to remove unbound antibody;
   (d) reacting the antigen/antibody complexes with an enzyme-labelled antihuman antibodies to form a sandwich complex;
   (e) separating the sandwich complex to remove unbound labelled antihuman antibodies; and
   (f) reacting the sandwich complex with a compound able to act as a substrate for the enzyme label such that the enzymatic reaction can be colorimetrically monitored; wherein all reagents used in steps (a) –(f) are stable at temperatures between 4° and 39° C.

2. A method of claim 1 wherein the antihuman antibodies have been labelled with alkaline phosphatase.

3. A method of claim 2 wherein the substrate is 5-bromo-4-chloro-3-indolyl phosphate toluidine.

4. A method according to claim 1 wherein the solid support comprises an inert flat surface upon which a multiplicity of separate areas have had spots of antigen immobilized thereto.

5. A method according to claim 4 wherein the flat inert solid support is divided into a multiplicity of quadrants each having an aliquot of antigen immobilized to a portion of the surface within each quandrant.

6. An immunoassay according to claim 1 wherein the saliva sample is diluted with a buffered saline solution containing nonfat dry milk.

7. A method according to claim 6 wherein the buffered saline solution contains a phosphate salt.

8. A method according to claim 7 wherein the nonfat milk comprises between 2–10% of the saline solution.

* * * * *

UNITED STATES PATENT AND TRADEMARK OFFICE
CERTIFICATE OF CORRECTION

PATENT NO. : 5,149,623
DATED : Sep. 22, 1992
INVENTOR(S) : Carlson et al.

It is certified that error appears in the above-identified patent and that said Letters Patent is hereby corrected as shown below:

ON THE TITLE PAGE:

After item [22] and before item [51] insert the following:

--Related U.S. Application Data

[63] Continuation-in-part of Ser. No. 153,902, filed Feb. 9, 1988, now abandoned.--

Signed and Sealed this

Ninth Day of November, 1993

*Attest:*

BRUCE LEHMAN

*Attesting Officer*  *Commissioner of Patents and Trademarks*